US008114646B2

(12) United States Patent
Martin et al.

(10) Patent No.: US 8,114,646 B2
(45) Date of Patent: Feb. 14, 2012

(54) METHOD FOR ULTRASONIC CELL REMOVAL

(75) Inventors: Gregory Roger Martin, Acton, ME (US); Allison Jean Tanner, Portsmouth, NH (US)

(73) Assignee: Corning Incorporated, Corning, NY (US)

(*) Notice: Subject to any disclaimer, the term of this patent is extended or adjusted under 35 U.S.C. 154(b) by 408 days.

(21) Appl. No.: 12/468,590

(22) Filed: May 19, 2009

(65) Prior Publication Data

US 2009/0298153 A1    Dec. 3, 2009

Related U.S. Application Data

(60) Provisional application No. 61/130,521, filed on May 30, 2008, provisional application No. 61/116,928, filed on Nov. 21, 2008.

(51) Int. Cl.
*C12N 13/00* (2006.01)
*C12M 1/00* (2006.01)

(52) U.S. Cl. .................................. 435/173.9; 435/308.1

(58) Field of Classification Search ............... 435/173.9, 435/308.1
See application file for complete search history.

(56) References Cited

U.S. PATENT DOCUMENTS

2007/0026516 A1   2/2007   Martin et al. ............... 435/297.5

FOREIGN PATENT DOCUMENTS

| JP | 1994141850(A) | 5/1994 |
|---|---|---|
| JP | 2005080606(A) | 3/2005 |
| JP | 2005160340(A) | 6/2005 |
| JP | 2006314204(A) | 11/2006 |
| WO | WO 85/01514 | 4/1985 |
| WO | 89/12676 | 12/1989 |
| WO | WO 89/12676 | 12/1989 |
| WO | 03/089581 A2 | 10/2003 |
| WO | WO 03/089581 | 10/2003 |
| WO | 2005/065419 A2 | 7/2005 |
| WO | WO 2005/065419 | 7/2005 |
| WO | 2007/094929 A2 | 8/2007 |
| WO | WO 2007/094929 | 8/2007 |
| WO | 2007/131337 A1 | 11/2007 |
| WO | WO 2007/131337 | 11/2007 |
| WO | 2008/004752 A1 | 1/2008 |
| WO | WO 2008/004752 | 1/2008 |

OTHER PUBLICATIONS

Kim, Hee Joong, et al, "Ultrasound-Mediated Transfection of Mammalian Cells", Human Gene Therapy 7: 1339-1346 (Jul. 10, 1996).

Hultstrom, J., et al., "Proliferation and Viability of Adherent Cells Manipulated by Standing-Wave Ultrasound in a Microfluidic Chip", Ultrasound in Med. & Biol., vol. 33, No. 1, pp. 145-151, 2007.
Lu, X., et al, "Ultrasound-induced cell detachment and gene transfection in adherent cells", Acoustics Research Letters Online, vol. 6(3), 195-200, 2005.
Pitt, William G., et al., "Ultrasound Increases the Rate of Bacterial Cell Growth", Biotechnology Progress, 2003; 19(3): 1038-1044.
Wamel, Annemieke van, et al., "Remote manipulation of Cells with Ultrasound and Microbubbles", 2004 IEEE Ultrasoncis Symposium, International Ultrasonics, Ferroelectrics, and Frequency Control Joint $50^{th}$ Anniversary Conference, 1094-1097, 2004.
Cousins, C.M., et al., "Clarification of plasma from whole human blood using ultrasound", Ultrasoncis 38, (2000), 654-656.
Chisti, Yusuf, "Sonobioreactors: using ultrasound for enhanced microbial productivity", Trends in Biotechnology, vol. 21, No. 2, Feb. 2003.
Takayama, Tadahiro, et al., "Low-intensity pulsed ultrasound stimulates osteogenic differentiation in ROS 17/2.8 cells", Life Sciences 80, (2007), 965-971.
Morita, Seiichi, et al., "Characterization and On-Line Monitoring of Cell Disruption and Lysis Using Dielectric Measurement", Journal of Bioscience and Bioengineering, vol. 88, No. 1, 78-84, 1999.
Hallow, Daniel M., "Ultrasonically targeted delivery into endothelial and smooth muscle cells in ex vivo arteries", Journal of Controlled Release, 118, (2007), 285-293.
Debavelaere-Callens, Dorothee, et al., "On the use of ultrasounds to quantify the longitudinal threshold force to detach osteoblastic cells from a conditioned glass substrate", Biomolecular Engineering 24, (2007), 521-525.
Ohl, Claus-Dieter, et al., Detachment and sonoporation of adherent HeLa-cells by shock wave-induced cavitation, Biochimica et Biophysica Acta, 1624, (2003), 131-138.
Kim, Hee Joong, et al, "Ultrasound-Mediated Transfection of Mammalian Cells", Human Gene Therapy 7: 1339-1346 (Jul. 10, 1996).
Hultstrom, J., et al., "Proliferation and Viability of Adherent Cells Manipulated by Standing-Wave Ultrasound In a Microfludic Chip", Ultrasound in Med. & Biol., vol. 33, No. 1, pp. 145-151, 2007.
Lu, X., et al, "Ultrasound-induced cell detachment and gene transfection in adherent cells", Acoustics Research Letters Online, vol. 6(3), 195-200, 2005.
Pitt, William G., et al., "Ultrasound Increases the Rate of Bacterial Cell Growth", Biotechnology Progress, 2003; 19(3): 1038-1044.
Wamel, Annemieke van, et al., "Remote manipulation of Cells with Ultrasound and Microbubbles", 2004 IEEE Ultrasonics Symposium, International Ultrasonics, Ferroelectrics, and Frequency Control Joint $50^{th}$ Anniversary Conference, 1094-1097, 2004.
Cousins, C.M., et al., "Clarification of plasma from whole human blood using ultrasound", Ultrasonics 38, (2000), 654-656.

(Continued)

*Primary Examiner* — Chih-Min Kam
(74) *Attorney, Agent, or Firm* — Susan S. Wilks (57) ABSTRACT

The present invention provides a method for treating cell culture vessels including multi-layer cell culture vessels with ultrasonic energy to dissociate cells growing on surfaces of cell culture vessels.

11 Claims, 7 Drawing Sheets

OTHER PUBLICATIONS

Chisti, Yusuf, "Sonobioreactors: using ultrasound for enhanced microbial productivity", Trends in Biotechnology, vol. 21, No. 2, Feb. 2003.

Takayama, Tadahiro, et al., "Low-intensity pulsed ultrasound stimulates osteogenic differentiation in ROS 17/2.8 cells", Life Sciences 80, (2007), 965-971.

Morita, Seiichi, et al., "Characterization and On-Line Monitoring of Cell Disruption and Lysis Using Dielectric Measurement", Journal of Bioscience and Bioengineering, vol. 88, No. 1, 78-84, 1999.

Hallow, Daniel M., "Ultrasonically targeted delivery into endothelial and smooth muscle cells in ex vivo arteries", Journal of Controlled Release, 118, (2007), 285-293.

Debavelaere-Callens, Dorothee, et al., "On the use of ultrasounds to quantify the longitudinal threshold force to detach osteoblastic cells from a conditioned glass substrate", Biomolecular Engineering 24, (2007), 521-525.

Ohl, Claus-Dieter, et al., Detachment and sonoporation of adherent HeLa-cells by shock wave-induced cavitation, Biochimica et Biophysica Acta, 1624, (2003), 131-138.

Altland, O.D., "Low-intensity ultrasound increases endothelial cell nitric oxide synthase activity and nitric oxide synthesis", Journal of Thrombosis and Haemostasis, 2, 637-643, (2004).

http://hyperphysics.phy-astr.gus.edu/hbase/sound/usound.html, printed Nov. 10, 2008.

http://www.nuncbrand.com/us/frame.aspx?ID=11490.

http://www.isbu.ac.uk/biology/enztech/ultrasonic.hml, printed Nov. 10, 2008.

http://www.iswork.com.sg/how%20ultrasonic%20cleaning%20works.htm, printed Nov. 12, 2008.

METHOD FOR ULTRASONIC CELL REMOVAL

CROSS REFERENCE TO RELATED APPLICATION

This Application claims the benefit of U.S. Provisional Application Ser. No. 61/130,521 filed May 30, 2008 and entitled "Method for Ultrasonic Cell Removal" and U.S. Provisional Application Ser. No. 61/116,928 filed Nov. 21, 2008 and entitled "Method for Ultrasonic Cell Removal" which is incorporated by reference herein.

FIELD

The present invention relates generally to a method for treating a cell culture vessel with ultrasonic energy to dissociate cells from a surface, allowing for cell removal in the absence of enzymes.

BACKGROUND

In vitro culturing of cells provides material necessary for research in pharmacology, physiology, and toxicology. Recent advances in pharmaceutical screening techniques allow pharmaceutical companies to rapidly screen vast libraries of compounds against therapeutic targets. These large-scale screening techniques require large numbers of cells grown and maintained in vitro. Maintaining these large numbers of cells requires large volumes of cell growth media and reagents and large numbers and types of laboratory cell culture containers and laboratory equipment. This activity is also labor intensive.

Cells are grown in specialized cell culture containers including roller bottles, cell culture dishes and plates, multi-well plates, microtiter plates, common (single-layer) flasks and multi-layered cell culture flasks and vessels. Cells in culture attach to and grow on the bottom surface(s) of the flask, immersed in a suitable sustaining media.

With the advent of cell-based high throughput applications, cell culture vessels have been developed to provide an increased surface area for cell growth while also providing necessary gas exchange. These systems also employ traditional cell culture vessels including common flasks, roller bottles, cell culture dishes, as well as multi-layered cell growth vessels including multi-layer flasks, multi-layer cell culture dishes, bioreactors, cell culture bags and the like, which may include specialized surfaces designed to enhance the cell culture parameters including growth density and differentiation factors.

In addition, cell-based high throughput applications have become automated. Automation permits manipulation of the cell culture vessel much like that performed by the manual operator. Further, flask vessels having multiple layers of cell growth surfaces are capable of producing greater yields of adherent cells than commonly known flasks that permit growth of cells on a single bottom wall. While these multiple layer vessels allow for the growth of large numbers of cells, they present special challenges in day to day use.

SUMMARY

Embodiments of the present invention provide a method for the treatment of cell culture vessels with ultrasonic energy to dissociate adherent cells from the cell growth surfaces of the multi-layer cell culture device.

Embodiments of the method of the present invention provide an ultrasonic treatment method for removing cells from a multi-layer cell culture container by treating the multi-layer cell culture container with ultrasonic energy. In embodiments, the method provide the steps of: growing cells in a cell culture container which may be a multi-layer cell culture container; treating the cell culture container with ultrasonic energy; and, removing dislodged cells from the cell culture container. During treatment, the multi-layer cell culture container may be open or closed and may contain liquid, which may be media or buffer, or not. The cell culture container may be repositioned and the treatment may be repeated if necessary.

Embodiments of the present invention also provide apparatus for providing ultrasonic energy to a multi-layer cell culture vessel having an ultrasonic transducer, a horn, a multi-layer cell culture vessel, and a base plate, where the ultrasonic transducer provides ultrasonic energy, through the horn, to the multi-layer cell culture vessel, which is held against the horn by a base plate. The apparatus may further have an acoustic coupler to conform to the shape of the multi-layer cell culture vessel and improve the acoustic coupling of the apparatus. The ultrasonic energy may be in the range of 1 to 100 kHz, for a period of from 1 second to 300 seconds.

BRIEF DESCRIPTION OF THE DRAWINGS

The invention is best understood from the following detailed description when read with the accompanying drawing figures.

DETAILED DESCRIPTION

Embodiments of the present invention relate to methods for using ultrasonic energy to dissociate cells from cell culture surfaces. In embodiments of the present invention, ultrasonic energy can be used to dislodge cells from cell culture surfaces of a multi-layer cell culture vessel having multiple layers of cell growth chambers in an integral multi-layer cell culture device. In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Increasingly, cell cultures, particularly adherent cell cultures, are grown in stacked, space saving high density containers which minimize incubator space and maximize cell culture growth surface, see for example US Publication No. 2007/0026516. As cell culture containers become more and more efficient, and the spaces within them become more and more restricted, the practical use of these containers becomes complicated by the need to move small quantities of liquids into and out of these containers.

A continuing challenge for the growth of adherent cells in culture is the process of dislodging these cells from the surfaces on which they grow. Methods exist in the art to expose the cells to enzymes such as trypsin, chymotrypsin, collagenase, etc. However, the use of these enzymes has limitations.

These enzymes may be animal-derived. Enzymes that are of animal origin bring a risk of contamination with, for example, viruses that can be isolated from the animal along with the enzyme. Regulatory requirements are increasingly stringent in the use of animal-derived components in the production of therapeutic agents, making animal-derived enzymes inappropriate for use in applications related to pharmaceutical development. Recombinant varieties of proteases may be available.

While these enzymes dissociate the cells from one another, and the substrate, they can also damage cells by cleaving cell surface proteins from the cells. Particularly when viable cells are the therapeutic agent, the cells must remain undamaged. Some cell types are very sensitive to proteases and will lose viability rapidly after enzyme treatment. Enzymes may be difficult to control, may damage cells, and may lead to cell line and stem cell instability and abnormal cell karyotypes in cultured cells.

In addition, with the advent of advanced cell culture surfaces having complex three dimensional structures, enzymatic treatment may not provide sufficient cell release. Therefore there is a need to provide a method for dislodging cells from a cell culture surface without the need for enzyme or other chemical treatment.

Non-enzymatic solutions of chelators such as phosphate-buffered saline with ethylenediaminetetraacetic acide (PBS-EDTA) may also be used to dissociate cells. However, these commonly do not dissociate cells from other cells in the monolayer culture. Cells may become detached from a substrate, but may remain attached to one another, allowing for cells to be released in clumps. Cell clumps usually require some additional mechanical or chemical (including enzymatic) manipulation such as repeated pipetting, to become a population of single cells.

When these chemical and enzymatic methods are used, the solutions must be washed away from the cells, and the cells must be concentrated by another method such as centrifugation or filtration. Ultimately, all of these steps add to the time and expense of chemical release of cells.

Cells may also be removed from a substrate by physically scraping the cells from the surface using a cell scraper. This method is not used very frequently because many cell culture vessels do not provide access for cell scrapers. The action of the cell scraper easily damages cells, which leads to release of proteases from within the damaged cells, resulting in more cell damage. Protease inhibitors can be used, along with scraping to mitigate this damage. The reagents are expensive. Cell scraping, then is also a multi-step time consuming and expensive technique for removing adherent cells from a cell culture surface.

Ultrasound has been used to assemble and join like materials through vibration, frictional heating and subsequent melting. Ultrasound is also used in many medical and biological applications. Ultrasound has been used in vitro to analyze the response of cells in culture, and to manipulate cells remotely. Other biological application of ultrasound include controlling cell movement in microfluidic channels, clarification of plasma from whole blood, targeting delivery of drugs, determination of adhesion force of cells to a substrate, sonoporation for gene transfection, and acceleration of cell differentiation.

While the generation of cavitation bubbles in ultrasonic water baths is commonly used to clean supplies, it can also be used to enhance microbial productivity, increase bacterial cell growth, and to remove cells from a culture device. However, the generation of cavitation bubbles can be harmful to cells, and is commonly used as a method for cellular disruption. Therefore, care must be taken in choosing ultrasonic frequencies to minimize damage to cells using cavition bubbles.

It may be possible to dissociate adherent cells from a cell culture surface by submersing the vessel in an ultrasonic water bath. However, this method may also be problematic. For example, submersion of cell culture vessels in water baths greatly increases the risk that contamination may occur.

In embodiments of the present invention, methods for dissociating cells from an adhesion substrate using resonant waves developed in the substrate through contact with ultrasonic impulses is provided. Apparatus for carrying out the methods are also provided. Using embodiments of these methods, there is no need to add additional components to the culture medium such as enzymes or chelators. In embodiments of the present invention, cell culture medium is removed from cells growing in a cell culture vessel which may be a multi-layer cell culture flask. In embodiments, the cells may be rinsed free of residual media components while still attached to the adhesion substrate using a buffer solution such as PBS. In additional embodiments, liquid, which may be media or buffer, may be present. In embodiments, cell culture vessel which may be a multi-layer flask is placed in a fixture where it is subjected to an ultrasonic frequency for a short period of time. Cells subjected to this ultrasonic frequency are released from the cell culture layers of the cell culture vessel. Cells may be collected by pouring them from the vessel, with no additional washing or concentrating steps necessary. In additional embodiments, additional rinses of the cell culture vessel may be undertaken to ensure complete removal of the cells from the cell culture vessel which may be a multi-layer flask.

In embodiments of the present invention, a multi-layer flask is provided. An embodiment of the multi-layer flask 100 of the present invention is illustrated in the partial cut-away perspective view shown in FIG. 1. The multi-layer flask 100 has an outer vessel body 101 defined by a top plate 110, a bottom tray (not shown), sidewalls 112, and end walls 114. Disposed within the flask 100 are individual cell growth chambers 111 as can be seen more clearly in the cut-away portion of FIG. 1. The individual cell growth chambers 111 are each defined by a bottom surface 113 and a top surface 115. The surfaces 113 and 115 are attached to the flask body 101 along the sidewalls 112 and end walls 114. Preferably, at least one bottom surface 113 within each chamber 111 is a gas permeable, liquid impermeable material capable of providing a surface for the growth of cells 117. The gas permeable, liquid impermeable material may provide the surface upon which cells attach, or the floor of the cell growth chamber, or it may be the opposite surface, or the ceiling of the cell growth chamber. The bottom surface 113, or the cell culture surface 113 may be flexible. Each top surface 115 may be a rigid, generally gas impermeable material that will provide support to the cell growth chamber 111. The surfaces of the multi-layer flask may be clear, opaque, colored or colorless. In an embodiment of the present invention, there are tracheal spaces 118 between each cell growth chamber 111. The opposing top surface 115 of the chamber 111 defines an upper wall to the cell growth chamber 111 as well as a bottom portion of a tracheal chamber 118. The tracheal chamber 118 is therefore inclusive of a gas permeable, liquid impermeable surface 113 of a first cell growth chamber and an opposing surface 115 of a second growth chamber 111. Supports 119 may also be present to provide structural support to integrally incorporate the surfaces 113 and 115 in forming growth chambers 111 in alternation with tracheal air spaces 118 within the unitary flask 101. Each cell growth chamber 111 therefore alternates with a tracheal chamber 118 in vertical successive orientation.

Figure 1:
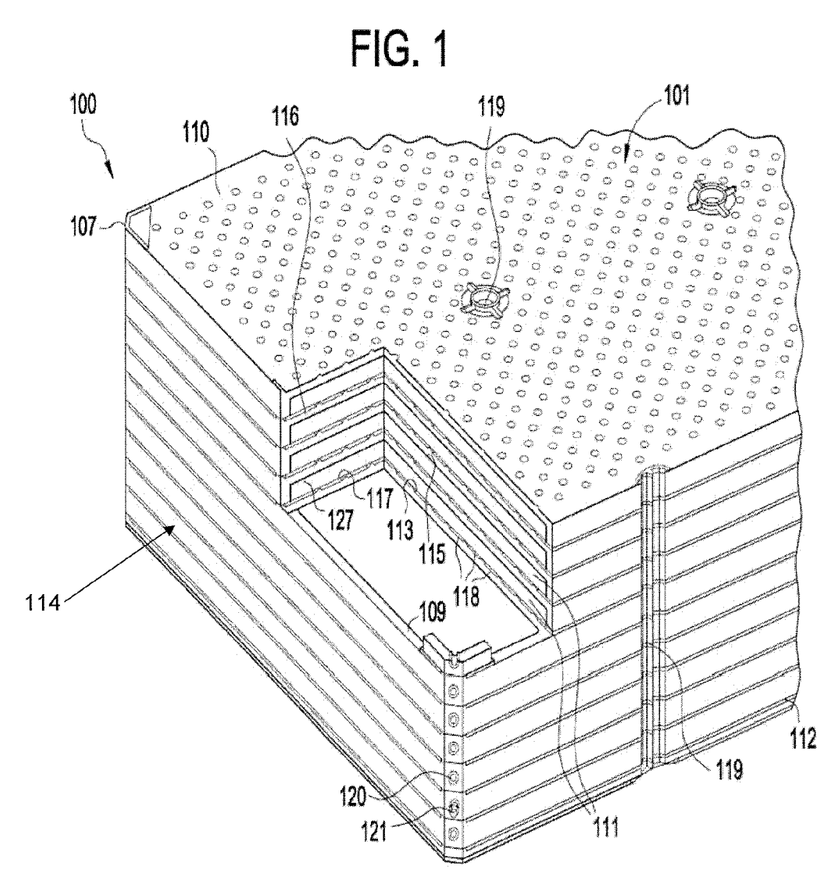
FIG. 1 shows an embodiment of a multi-layer cell culture vessel.

In one embodiment of the present invention, the individual cell growth chambers 111 permit cellular growth on gas permeable membranes 113 such that multiple cell growth chambers 111 are integral with the body 101 of the multi-layer flask 100 and are capable of being completely filled with nutrient media for the growth of cells. The series of tracheal air spaces 118 through the multi-layer flask 100 provide gaseous communication between the cells 117 growing on gas permeable surfaces 113, in media 127 in the individual cell growth chambers 111 inside the multi-layer flask, and the external environment. The tracheal spaces 118 allow oxygenation of media located within cell growth chambers 111 through the gas permeable surfaces 113. Further, the tracheal chambers 118 may take the form of any air gap or space, and do not allow entrance of liquid. As a result, a rigid cell culture multi-layer flask 100 having multiple growth chambers 111, alternating with tracheal spaces 118, is cooperatively constructed to afford the benefit of equivalent gaseous distribution to a large volume of cells 117.

Gas permeable membrane 113 can be affixed to supports 119 and side walls 112 by any number of methods including but not limited to adhesive or solvent bonding, heat sealing or welding, compression, ultrasonic welding, laser welding and/or any other method commonly used for generating seals between parts. Laser welding around the circumference of the membrane 113 is preferred to establish a hermetic seal around the membrane region such that the membrane is flush with and fused to the face of the supports 119 such it becomes an integral portion of the interior surface of the multi-layer flask. Once the gas permeable membrane 113 is adhered to the sidewalls and endwalls, the top plate 110 and bottom tray 120 may be joined. The bottom tray 120 and top plate 110 may be injection molded. Various sizes and shapes of the supports 119 may be incorporated to facilitate positioning of the membranous layers 113 for cell culture 117 within the cell culture vessel 100.

Gas permeable, liquid impermeable membranes 113 (see FIG. 1) may be made of one or more membranes known in the art. Membranes typically are made of suitable materials that may include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. As manufacturing and compatibility for the growth of cells permits, various polymeric materials may be utilized. For its known competency, then, polystyrene may be a preferred material for the membrane (of about 0.003 inches in thickness, though various thicknesses are also permissive of cell growth). As such, the membrane may be of any thickness, preferably between about 25 and 250 microns, but ideally between approximately 25 and 125 microns.

In embodiments of the present invention, these gas permeable, liquid impermeable membranes 113 are thin and flexible enough to vibrate in response to the application of ultrasonic frequencies to the multi-layer flask. This vibration, introduced into the cell culture surfaces of the multi-layer flask, releases adherent cells from the cell culture surfaces.

The multi-layer flask 100 of the present invention may be made by any number of acceptable manufacturing methods well known to those of skill in the art. In an embodiment of a method, the multi-layer flask 100 is assembled from a collection of separately injection molded parts. Although any polymer (such as polystyrene, polycarbonate, acrylic, polystyrene, or polyester) suitable for molding and commonly utilized in the manufacture of laboratory ware may be used, polystyrene is preferred. Although not required, for optical clarity, it is advantageous to maintain a thickness of no greater than 2 mm. The separate parts may be assembled by any number of methods including but not limited to: adhesive or solvent bonding, heat sealing or welding, compression, ultrasonic welding, laser welding and/or any other method commonly used for generating seals between parts such that it becomes an integral portion of the interior surface of the multi-layer flask. The top plate 110 and bottom tray may be aligned and joined, such as by laser welding.

In an embodiment, parts are held together and are adhesive bonded along the seam, ultrasonically welded, or laser welded, bonded using heat platens or by any other methods. Preferably, laser welding equipment is utilized in a partially or fully automated assembly system. The top plate and tray are properly aligned while a laser weld is made along the outer periphery of the joint.

Advantageously and in order to enhance cell attachment and growth, the surfaces internal to the multi-layer flask 100, including the membrane layer, may be treated to enable cell growth. Treatment may be accomplished by any number of methods known in the art which include coatings, plasma discharge, corona discharge, gas plasma discharge, ion bombardment, ionizing radiation, and high intensity UV light.

In an alternative embodiment, an individual cell growth chamber may be bounded on one side by a layer of gas permeable membrane 110, attached in a liquid impermeable manner to sidewalls 112 and on another side by a top surface that is a rigid layer, to provide a more rigid element to the individual cell culture growth chamber 111 and the multi-layered flask as a whole. For example, an individual cell growth chamber 111, bounded on a top side by a rigid layer 115, on its edges by sides, and on a bottom side by a gas permeable membrane. This individual cell growth chamber 111 can be stacked on top of another such individual cell growth chamber 111, where the top portion of a rigid layer 115 of one individual cell growth chamber 111 forms a support structure that defines tracheal spaces underneath a gas permeable membrane 113 of the adjacent individual cell growth chamber. In an embodiment, individual cell culture chambers can be assembled into a larger multi-layer cell culture vessel. These individual layers can be snapped together, or otherwise attached to each other using any attachment method known in the art.

FIG. 1 also illustrates alternating layers of tracheal air spaces 118 and individual cell growth chambers 111 which form the interior of flask 100. The individual cell growth chambers 111 are defined by liquid impermeable, gas permeable membranes 113 attached in a liquid-impermeable manner to the sidewalls and endwalls of the cell culture vessel. Cell growth media 127 is contained between the membranes 113 and cells grow on the liquid-surface of these membranes 113. In this embodiment, the cell growth chamber 111 may be formed by two layers of gas permeable membrane attached in a liquid impermeable manner to sidewalls 112 to form an individual cell growth chamber 111. Tracheal air spaces 118 form layers between the gas permeable membranes, forming air pockets to allow the gas permeable membranes 113 to exchange air into the cell growth media 127. In this embodiment, tracheal air spaces are supported by supports 119 which separate and support the layers of gas permeable membrane 113 which form individual cell growth chambers 111. A preferred embodiment would include a membrane 113 that is additionally durable for manufacture, handling, and manipulation of the multi-layer flask. While a multi-layer flask is illustrated, it will be understood that embodiments of the present invention will also be applicable in single-layer cell culture vessels. Therefore, it will be understood that present invention includes single-layer vessel embodiments and multi-layer vessel embodiments.

Figure 2:
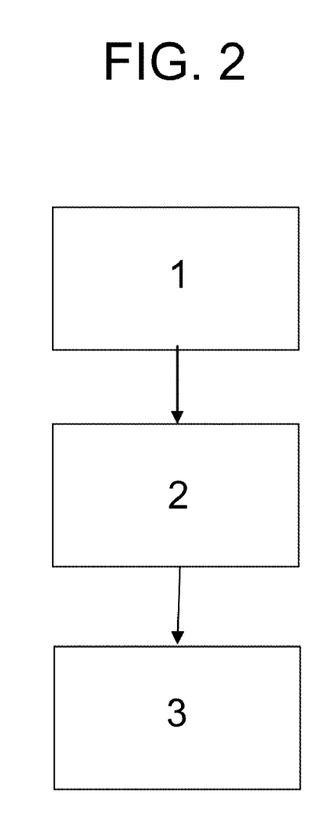
FIG. 2 is a flowchart illustrating an embodiment of the method of the present invention.

FIG. 2 shows a flowchart of an embodiment of the method of the present invention. In FIG. 2, In STEP 1, cells are grown in a cell culture vessel, in STEP 2, the cell culture vessel is treated with ultrasonic energy to release cells from the growth surfaces of the cell culture vessel, and in STEP 3, cells are removed from the cell culture vessel. In additional embodiments, before STEP 2, liquid, cell culture media or buffer, may be removed from the cell culture vessel. This may occur by pouring the media from the cell culture vessel. This may result in some residual liquid remaining inside the vessel during treatment, without adversely affecting the results. In additional embodiments, the cell culture vessel in STEP 2 may be entirely or partially filled with media or buffer during the treatment. The vessel may be capped, uncapped or loosely capped during the treatment of STEP 2. In embodiments, the cell culture vessel may be a single layer or multi-layer cell culture vessel.

Figure 3:
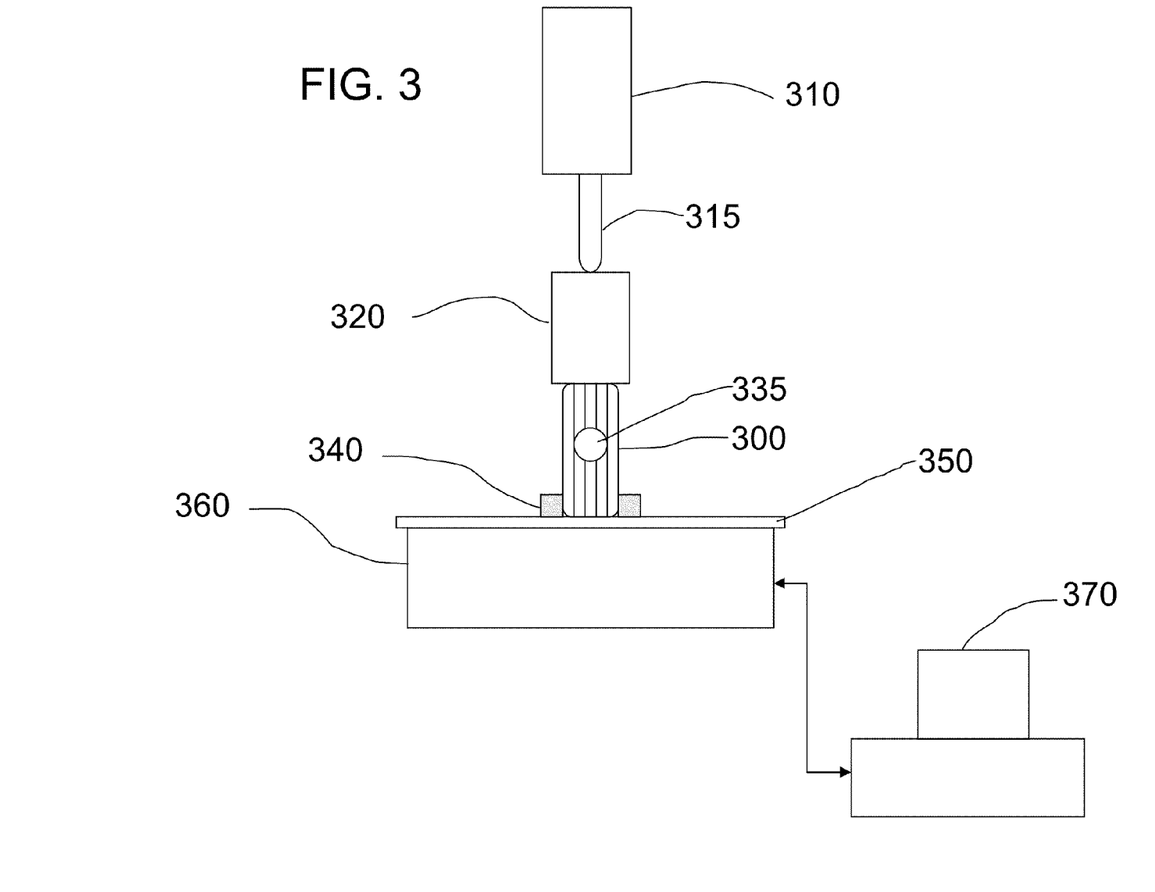
FIG. 3 illustrates an embodiment of the ultrasonic energy delivery system of the present invention.

FIG. 3 illustrates an embodiment of the ultrasonic treatment apparatus of the present invention. FIG. 3 shows an ultrasonic transducer 310 coupled by a coupling arm 315 to a horn 320 which drops down to couple to the cell culture apparatus 300 to be treated. The horn may be structured and arranged to fit snugly against the multi-layer cell culture vessel. If the horn is structured and arranged to fit snugly against the multi-layer cell culture device, ultrasonic energy may be applied more efficiently to the multi-layer cell culture vessel. FIG. 3 illustrates a multi-layer cell culture vessel, but this could be any cell culture vessel. The cell culture vessel may be in a side-lying position, as shown in FIG. 3, or may be placed into the apparatus in any orientation.

Figure 4:
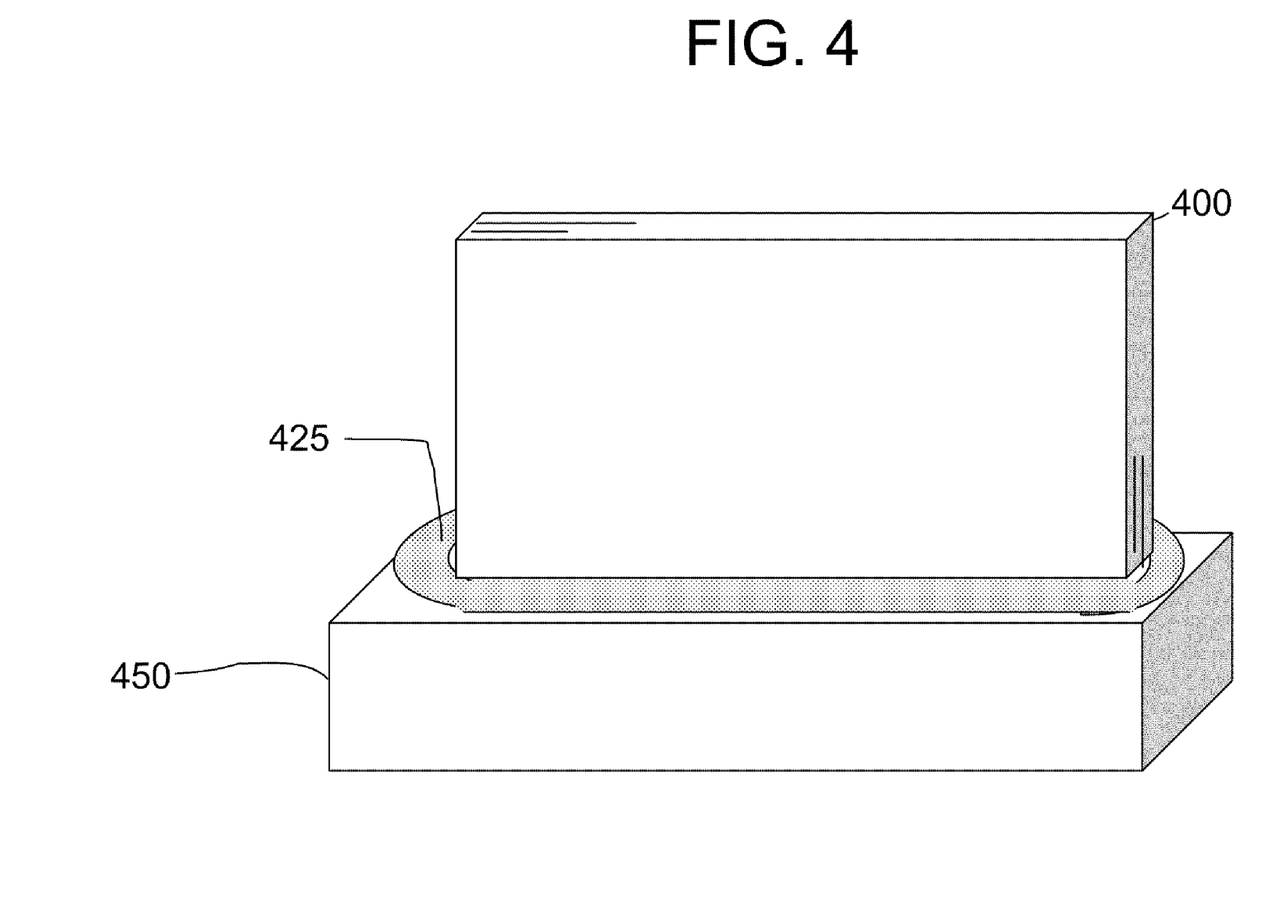
FIG. 4 illustrates an embodiment of a multi-layer flask coupled to an acoustic generator by an acoustic coupling device.

Because a multi-layer cell culture vessel has multiple layers, the coupling between the multi-layer cell culture vessel and the ultrasonic generator may need to be considered to ensure that all of the layers of the cell culture device are treated. Treating the multi-layer cell culture vessel in a side-lying position, as shown in FIG. 3 and FIG. 4, may be more efficient, for example. In a side-lying position, the ultrasonic generator may provide ultrasonic energy to each of the multiple layers of cell culture efficiently. In an alternative embodiment, ultrasonic energy may be provided to the sides of the cell culture apparatus, which may include the side which contains a neck and/or cap, and the side opposite the side containing a neck and/or cap. For example, ultrasonic energy may be provided while the multi-layer cell culture device is in the orientation that it would normally hold during cell culture, and an ultrasonic generator may be brought to the cell culture device from one or both sides of the device. Or, in additional embodiments, providing an acoustic coupler to improve the coupling between the ultrasonic generator and the multi-layer cell culture device may improve the efficiency of the ultrasound treatment by ensuring that a maximal amount of ultrasonic energy is transferred between the ultrasonic generator or transducer and the multi-layer cell culture vessel.

The cell culture vessel may have a cap 335, which may be present or not present during ultrasonic treatment. In addition, the cap 335 may be tightly closed during ultrasonic treatment, or loosely applied. A fixture 340 may be present to hold the cell culture vessel in place during ultrasonic transmission. The fixture 340 may include an acoustic coupling device or acoustic coupler. The fixture 340 may hold the cell culture vessel against a base plate 350. The base plate may be affixed to a measuring device 360 which may communicate to a computer 370 to allow the operator to monitor the parameters of the ultrasonic treatment.

To apply the ultrasonic treatment to the cell culture vessel, the ultrasonic transducer 310 is coupled to the cell culture vessel to be treated 300 by lowering the horn 320 until it touches the cell culture vessel 300. The ultrasonic transducer 310 delivers ultrasonic energy to the cell culture vessel 300 for a period of time to release cells. After the treatment, the horn 320 is raised, the cell culture vessel 300 is removed from the apparatus, and further processed. For example, cells dislodged from the cell culture container surface may be removed from the cell culture container. Cells that are dislodged are cells that float freely in media or buffer in the container, and are not stuck to the cell growth surfaces of the cell culture container.

FIG. 4 illustrates an embodiment the multi-layer flask 400 which may be held against the fixture or base plate 450 by an acoustic coupling device 425. In embodiments, the acoustic coupling device comprises a rubber pad between the base plate and the cell culture container, or between the horn and the cell culture container (not shown). This acoustic coupling device is structured and arranged to improve the acoustic bond between the ultrasonic generator and the cell culture vessel, or to between the base plate and the cell culture vessel. While a rubber pad is disclosed, any structure that improves the acoustic bond between the ultrasonic generator and the cell culture vessel or between a base plate or other stationary surface and the cell culture vessel may be an acoustic coupling device 425.

Figure 5:
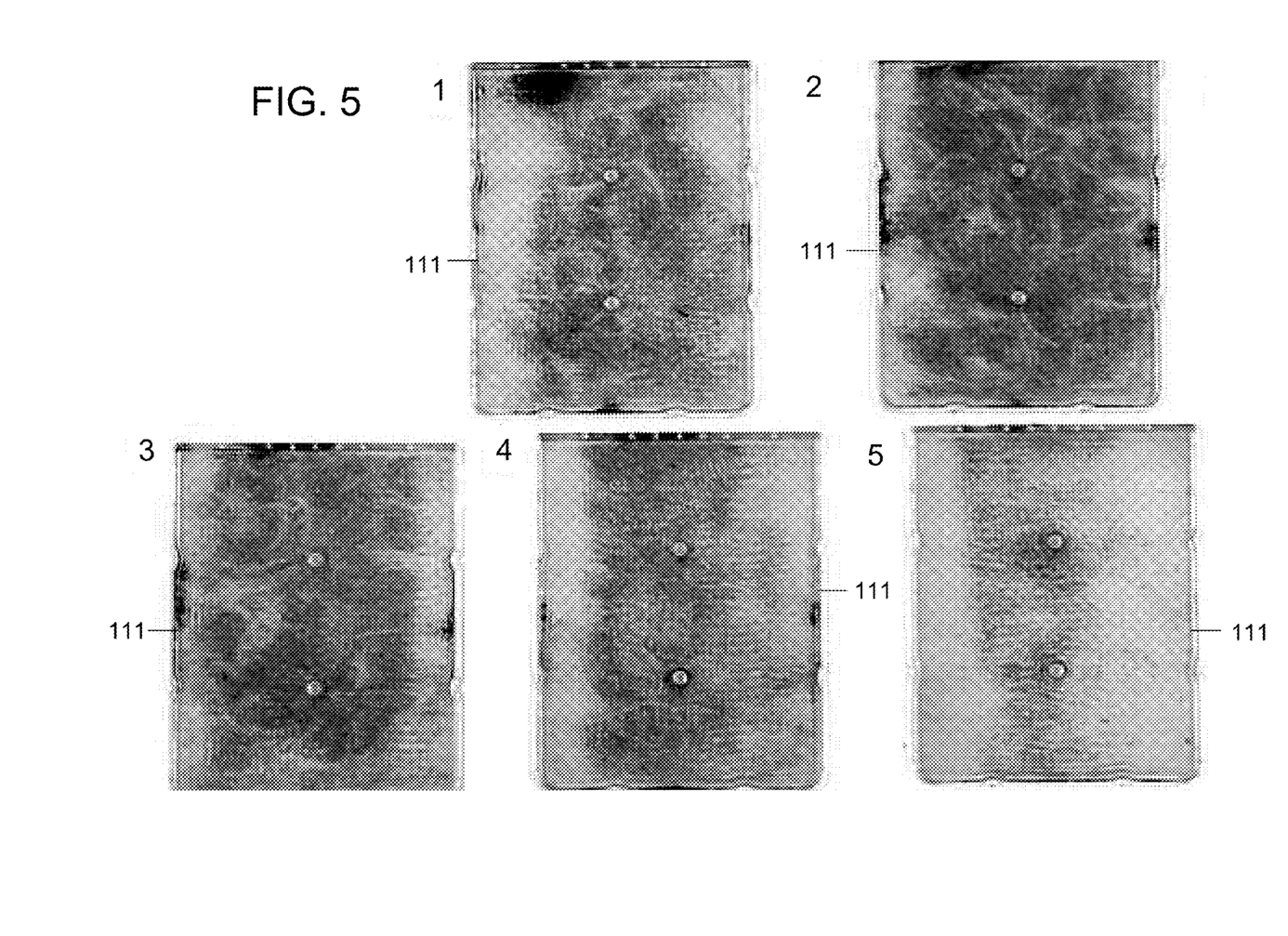
FIG. 5 shows the first 5 flaskettes of a multi-layer flask, after treatment with an embodiment of the method of the present invention, stained to show cells remaining attached to the cell growth surface.
Figure 6:
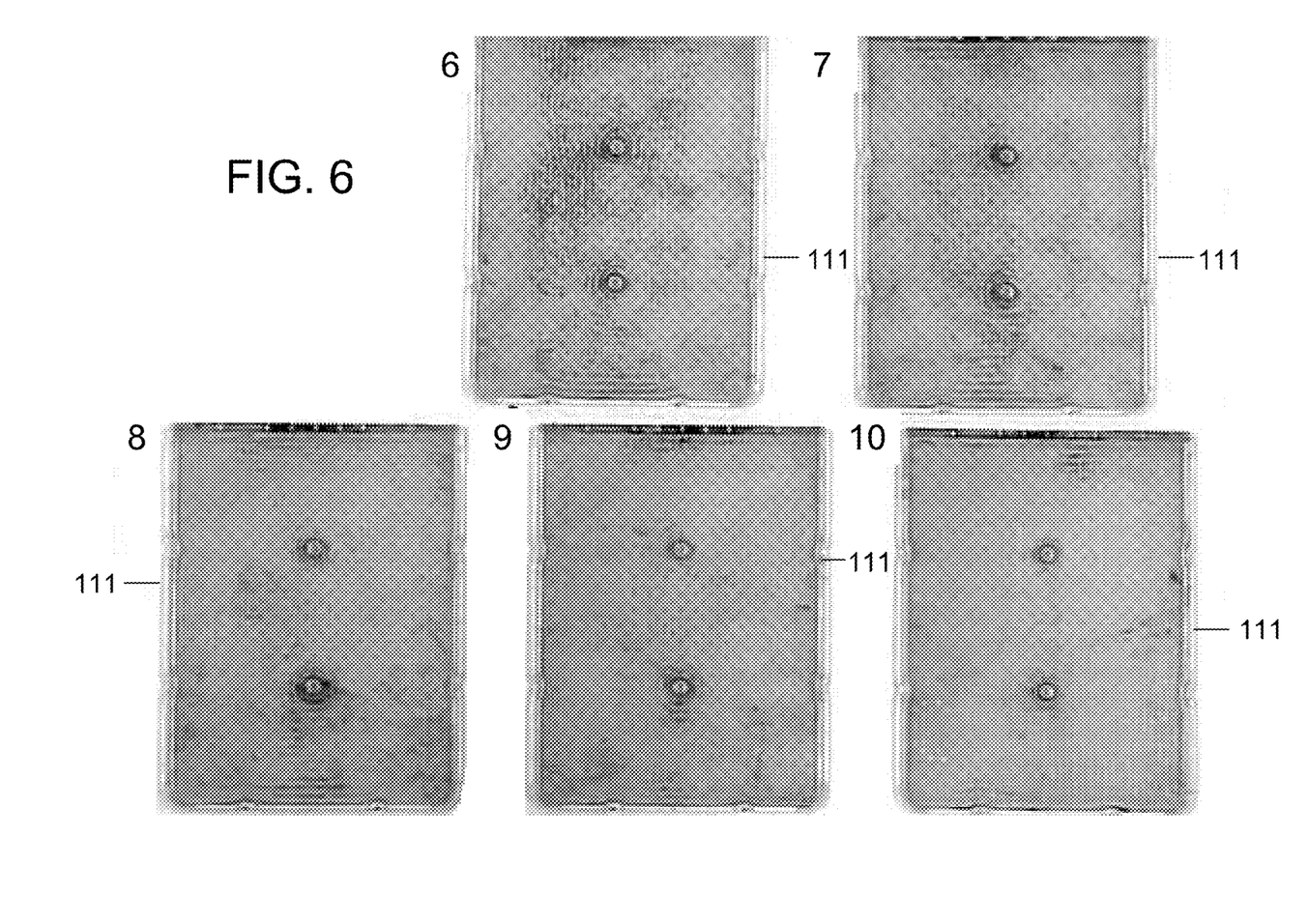
FIG. 6 shows the second 5 flaskettes of a multi-layer flask, after treatment with an embodiment of the method of the present invention, stained to show cells remaining attached to the cell growth surface.

FIGS. 5 and 6 are photographs of flaskettes of disassembled multi-layer cell culture vessels after the vessels (assembled) were treated according to embodiments of the present invention with ultrasonic energy. The flaskettes were stained to show the removal of cells from the vessels. The flaskettes are successive cell culture chambers 111 numbered 1 through 10, representing the 10 successive flaskettes in the assembled ten-layer cell culture vessel. Flaskette number 5, for example, is in the middle of the multi-layer cell culture vessel, while flaskettes 1 and 10 are on the top and bottom, respectively, of the multi-layer cell culture vessel. For example, an individual cell growth chamber 111 is bounded on a top side by a rigid layer 115, and on a bottom side by a gas permeable membrane 113. Cells were grown on the gas permeable membrane 113. Cells that remained attached to the gas permeable membrane of an individual growth chamber were stained using standard crystal violet staining techniques, so that cells appear dark in FIGS. 5 and 6.

FIG. 5 shows the first 5 flaskettes show cells remaining adhered on the cell growth surface of the flaskette (or lack of cells adhering to the cell growth surface) after ultrasonic treatment. FIG. 6 shows the second 5 flaskettes, stained to show cells remaining adhered on the cell growth surface of the flaskette. The flask illustrated in FIGS. 5 and 6 was treated with an ultrasonic treatment at 20 kHz for 30 seconds at 15% or 20% amplitude applied using a standard horn from an ultrasonic welding generator which may be built to match the surface area of contact on the flask and a fixture that holds the flask during the ultrasonic impulse. The fixture may be a part of the horn, or may be a separate device which connects the ultrasonic generator to the horn, or to the multi-layer cell culture device. In embodiments of the present invention, suitable ultrasonic treatments may include ultrasonic energy in the range of 1-40 Hz, 10-40 Hz, 15-40 Hz, or 15-30 Hz. The energy may be applied for 10-30 seconds, and may be applied more than once. For example, ultrasonic energy may be applied to one side of the article to be treated, the article may then be moved or flipped or realigned in the apparatus and a second treatment may occur. Or, in other embodiments, ultrasonic energy may be applied from two sides at the same time, eliminating the step of flipping or realigning and re-treating the article. In embodiments, suitable amplitudes range from 10 to 20%. In some embodiments, a rubber pad (see 425, FIG. 4) may be applied to the horn to allow for better transmission of ultrasonic energy from the ultrasonic generator through the horn, to the cell culture vessel. This rubber pad is an acoustic coupling device, structured and arranged to improve the acoustic bond between the ultrasonic generator and the multi-layer cell culture device, or between the base plate and the cell culture vessel. While a rubber pad is disclosed, any structure that improves the acoustic bond between the ultrasonic generator and the cell culture vessel or between a base plate or other stationary surface and the cell culture vessel may be an acoustic coupling device.

The Flask illustrated in FIGS. 5 and 6 contained no media during treatment and the cap was tightly affixed to the flask during treatment. While the flask contained no media and had a tightly affixed cap during treatment, this experiment has been repeated using flasks that contained media during treatment with an embodiment of the method of the present invention, with the cap on, and with the cap removed, and combinations of these with satisfactory results (results not shown). Embodiments of methods of the present inventions were effective in the presence of media, in the absence of media, with a tight cap, with a loose cap, and with no cap. In embodiments of the present invention, after the ultrasonic treatment step, the flask may also be rapped or impacted against a laboratory bench. The flask shown in FIG. 5 and FIG. 6 was rapped against a laboratory bench twice (two impacts) before the flask was rinsed and disassembled. Cells were then removed from the flask and stained with a vital stain to indicate percent cell viability. Cells removed from this flask after ultrasonic treatment were 92.2% viable. As can be seen from FIGS. 5 and 6, each of the flaskettes of the multi-layer cell culture device showed nearly complete cell removal after treatment with an embodiment of the method of the present invention.

Figure 7:
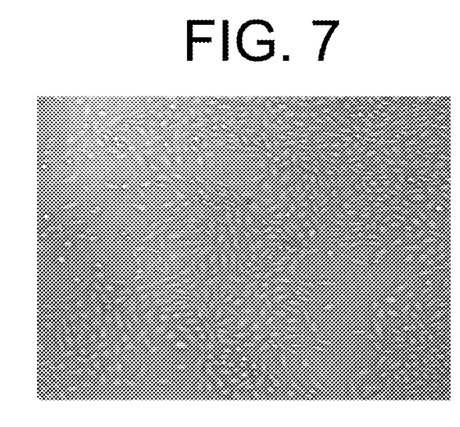
FIG. 7 is a photomicrograph of CHOK1 cells dissociated from a layer of gas permeable polystyrene film of a multi-layer flask, before treatment with an embodiment of the method of the present invention.
Figure 8:
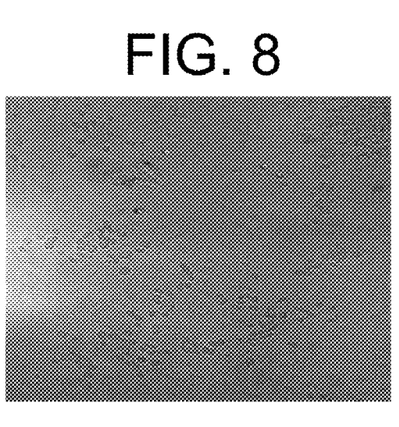
FIG. 8 is a photomicrograph of an adherent monolayer of CHOK1 cells growing on a layer of gas permeable polystyrene film of a multi-layer flask, after treatment with an embodiment of the method of the present invention.

FIG. 7 is a photomicrograph of an adherent monolayer of CHOK1 cells growing on a layer of gas permeable polystyrene film of a multi-layer flask, before treatment with an embodiment of the method of the present invention. FIG. 8 is a photomicrograph of the adherent monolayer of CHOK1 cells growing on a layer of gas permeable polystyrene film of a multi-layer flask, after treatment with an embodiment of the method of the present invention. As can be seen in FIGS. 7 and 8, most of the cells that were adherent on the cell growth surface prior to treatment with methods of the present invention are no longer adherent on the cell growth surface after treatment. FIG. 8 shows some rounded cells which remained attached to the cell culture surface after treatment, but most of the cells have lifted away from the surface and are floating in the residual fluid within the flaskette.

Figure 9:
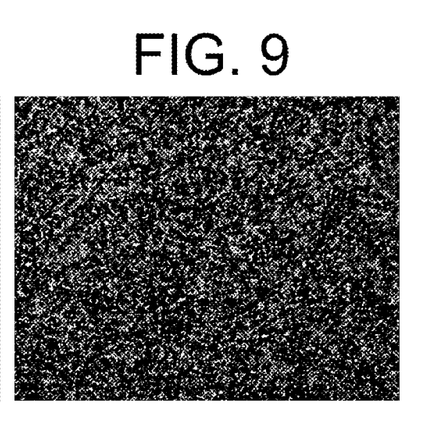
FIG. 9 is an image of cells ultrasonically released from a multi-layer flask, reseeded onto a standard T-175 flask to show the viability of cells treated according to an embodiment of the present invention.

FIG. 9 is an image of cells ultrasonically released from a multi-layer flask, reseeded and grown to confluence (over-confluent) on a standard T-175 flask to show the viability of cells treated according to an embodiment of the present invention, removed from the multi-layer cell growth vessel and reestablished in a fresh vessel. This establishes that the treated cells are viable.

EXAMPLES

Cell Culture

Adherent CHOK1 cells were cultured in Dulbecco's Modified Eagle's Medium (DMEM media) with 10% fetal bovine serum at 37 degrees C. in a multi-layer flask until a monolayer was achieved.

Cells removed from multi-layer flasks according to embodiments of the present invention were reseeded onto a standard T-175 flask to and allowed to grow to confluency (and over confluency) in DMEM media with 10% fetal bovine serum to generate the image of FIG. 9.

Ultrasonic Treatment

A multi-layer flask was placed in a side-lying position on a fixture beneath an ultrasonic horn after emptying the vessel of medium and washing the cells with PBS. The ultrasonic frequency was 20 KHz, and the amplitude 20%. A pulse was generated for 30 seconds by a Branson 2000 Ultrasonic welder on the first side before the vessel was turned and the pulse generated for another 30 seconds on the second side. Cells were visualized using light microscopy before and after the ultrasonic pulses to determine whether the cells had been dislodged from the adhesion substrate. Cells were poured from the vessel and viability determined to be 98%.

Flaskette Staining

After ultrasonic treatment, the multi-layer flask was disassembled into individual flaskettes, or individual cell culture chambers. After the dissociated cells were removed from the vessel, any remaining adherent cells were stained with crystal violet. Crystal violet was added to the vessel, and the vessel rocked to coat the cell culture surfaces. The stain was left in place for 5 minutes, then rinsed from the vessel with water. The vessel was allowed to dry before the layers were pulled apart to visualize individual layers.

While cells were removed from the flexible gas permeable films (cell culture surfaces) of the multi-layer flask, cells growing on the opposite rigid plastic sides of the flaskettes were not removed using these ultrasonic treatments (data not shown).

The adhesion substrates within the flaskettes were stained with crystal violet to detect cells remaining on the surface. Crystal violet was added to the vessel, and the vessel rocked to coat the cell culture surfaces. The The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The invention claimed is:

1. An ultrasonic treatment method for removing cells from a multi-layer cell culture container comprising:
   a. growing cells in a multi-layer cell culture container;
   b. treating the multi-layer cell culture container with ultrasonic energy;
   c. removing dislodged cells from the multi-layer cell culture container.

2. The method of claim 1 further comprising impacting the multi-layer cell culture container.

3. The method of claim 1 wherein the cell culture container contains media.

4. The method of claim 3 wherein the media has been removed from the multi-layer cell culture container.

5. The method of claim 1 wherein the multi-layer cell culture container is closed.

6. The method of claim 1 wherein the multi-layer cell culture container is open.

7. An apparatus for providing ultrasonic energy to a multi-layer cell culture vessel comprising:
   an ultrasonic transducer;
   a horn;
   a multi-layer cell culture vessel; and,
   a base plate,
   wherein the ultrasonic transducer provides ultrasonic energy, through the horn, to the multi-layer cell culture vessel and the multi-layer cell culture vessel is held against the horn by the base plate.

8. The apparatus of claim 7 further comprising an acoustic coupler to couple the horn to the multi-layer cell culture vessel.

9. The apparatus of claim 8 further comprising an acoustic coupler to couple the base plate to the multi-layer cell culture vessel.

10. The apparatus of claim 8 further comprising a fixture to support the multi-layer cell culture vessel against the base plate.

11. The apparatus of claim 8 wherein the horn is structured and arranged to fit against the multi-layer cell culture vessel.

* * * * *